United States Patent [19]
Brust et al.

[11] Patent Number: 6,120,990
[45] Date of Patent: Sep. 19, 2000

[54] IMMUNOCHEMICAL DETERMINATION OF MULTIVALENT ANALYTES

[75] Inventors: Stefan Brust; Hans-Peter Hauser; Stefan Knapp; Helmut Peters, all of Marburg, Germany

[73] Assignee: Dade Behring Marburg GmbH, Marburg, Germany

[21] Appl. No.: 09/090,190

[22] Filed: Jun. 4, 1998

[30] Foreign Application Priority Data

Jun. 4, 1997 [DE] Germany ............... 197 23 463

[51] Int. Cl.⁷ .................. C12Q 1/70; C12Q 1/04
[52] U.S. Cl. ................ 435/5; 435/7.32; 436/518
[58] Field of Search ............ 435/5, 7.94, 7.32; 436/518

[56] References Cited

U.S. PATENT DOCUMENTS

| | | | |
|---|---|---|---|
| 5,322,769 | 6/1994 | Bolling et al. | 435/5 |
| 5,480,972 | 1/1996 | Avgioglu et al. | 435/172.3 |
| 5,496,934 | 3/1996 | Shoseyov et al. | 536/23.7 |

FOREIGN PATENT DOCUMENTS

| | | |
|---|---|---|
| 0 187 041 | 7/1986 | European Pat. Off. . |
| 0 307 149 | 1/1993 | European Pat. Off. . |

OTHER PUBLICATIONS

Knapp et al., Biotechniques, A Simple Water Level Detection Device, vol. 8, No. 3 (1990), p. 281.

*Primary Examiner*—Donna C. Wortman
*Attorney, Agent, or Firm*—Foley & Lardner

[57] ABSTRACT

The present invention is directed to an immunochemical method for qualitatively or quantitatively detecting an analyte in which a first and a second binding component are contacted with the analyte, followed by detection of the binding of the binding components to the analyte. According to the invention, both of the binding components are prepared recombinantly in the same host using different vectors (V1 and V2) for expressing fusion proteins, with the first binding component being expressed as a fusion protein F1 in vector V1 and the second binding component being expressed as a fusion protein F2 in vector V2. The novel method, which can also be employed for simultaneously determining several analytes, is more sensitive and specific than prior known methods.

21 Claims, 4 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 300 base pairs
        (B) TYPE: nucleic acid
        (C) STRANDEDNESS: both
        (D) TOPOLOGY: circular (ii) MOLECULE TYPE: cDNA (ix) FEATURE:
        (A) NAME/KEY: CDS
        (B) LOCATION: 1..300

(xi) SEQUENCE DESCRIPTION: SEQ ID NO:1:

```
TTA TTG TCT GGT ATA GTG CAG CAG CAG AAC AAT TTG CTG AGG GCT ATT        48
Leu Leu Ser Gly Ile Val Gln Gln Gln Asn Asn Leu Leu Arg Ala Ile
 1               5                  10                  15

GAG GCG CAA CAG CAT CTG TTG CAA CTC ACA GTC TGG GGC ATC AAG CAG        96
Glu Ala Gln Gln His Leu Leu Gln Leu Thr Val Trp Gly Ile Lys Gln
                20                  25                  30

CTC CAG GCA AGA ATC CTG GCT GTG GAA AGA TAC CTA AAG GAT CAA CAG       144
Leu Gln Ala Arg Ile Leu Ala Val Glu Arg Tyr Leu Lys Asp Gln Gln
            35                  40                  45

CTC CTG GGG ATT TGG GGT TGC TCT GGA AAA CTC ATT TGC ACC ACT GCT       192
Leu Leu Gly Ile Trp Gly Cys Ser Gly Lys Leu Ile Cys Thr Thr Ala
        50                  55                  60

GTG CCT TGG AAT GCT AGT TGG AGT AAT AAA TCT CTG GAA CAG ATT TGG       240
Val Pro Trp Asn Ala Ser Trp Ser Asn Lys Ser Leu Glu Gln Ile Trp
 65                  70                  75                  80

AAT AAC ATG ACC TGG ATG GAG TGG GAC AGA GAA ATT AAC AAT TAC ACA       288
Asn Asn Met Thr Trp Met Glu Trp Asp Arg Glu Ile Asn Asn Tyr Thr
                85                  90                  95

AGC TTA ATA CAC                                                        300
Ser Leu Ile His
            100
```

(2) INFORMATION FOR SEQ ID NO:2:

(i) SEQUENCE CHARACTERISTICS:
        (A) LENGTH: 100 amino acids
        (B) TYPE: amino acid
        (D) TOPOLOGY: linear (ii) MOLECULE TYPE: protein (xi) SEQUENCE DESCRIPTION: SEQ ID NO:2:

```
Leu Leu Ser Gly Ile Val Gln Gln Asn Asn Leu Leu Arg Ala Ile
 1               5                  10                  15

Glu Ala Gln Gln His Leu Leu Gln Leu Thr Val Trp Gly Ile Lys Gln
                20                  25                  30

Leu Gln Ala Arg Ile Leu Ala Val Glu Arg Tyr Leu Lys Asp Gln Gln
                35                  40                  45

Leu Leu Gly Ile Trp Gly Cys Ser Gly Lys Leu Ile Cys Thr Thr Ala
            50                  55                  60

Val Pro Trp Asn Ala Ser Trp Ser Asn Lys Ser Leu Glu Gln Ile Trp
 65                 70                  75                  80

Asn Asn Met Thr Trp Met Glu Trp Asp Arg Glu Ile Asn Asn Tyr Thr
                85                  90                  95

Ser Leu Ile His
            100
```

(2) INFORMATION FOR SEQ ID NO:3:

(i) SEQUENCE CHARACTERISTICS:
        (A) LENGTH: 408 base pairs
        (B) TYPE: nucleic acid
        (C) STRANDEDNESS: both
        (D) TOPOLOGY: circular (ii) MOLECULE TYPE: cDNA (ix) FEATURE:
        (A) NAME/KEY: CDS
        (B) LOCATION: 1..405

(xi) SEQUENCE DESCRIPTION: SEQ ID NO:3:

```
TGT GTC TCG TGC ACA ACC GTG TGT CCG CAC GCC GGG AAG GCC AAA GCG         48
Cys Val Ser Cys Thr Thr Val Cys Pro His Ala Gly Lys Ala Lys Ala
 1               5                  10                  15

GAA AAG GTA GAG TGC GCG TTG AAG GGA GGT ATC TTT CGG GGT ACG CTA         96
Glu Lys Val Glu Cys Ala Leu Lys Gly Gly Ile Phe Arg Gly Thr Leu
                20                  25                  30

CCT GCG GCC GAT TGC CCG GGA ATC GAT ACG ACT GTG ACG TTC AAC GCG        144
Pro Ala Ala Asp Cys Pro Gly Ile Asp Thr Thr Val Thr Phe Asn Ala
            35                  40                  45

GAT GGC ACT GCG CAA AAG GTA GAG CTT GCC CTT GAG AAG AAG TCG GCA        192
Asp Gly Thr Ala Gln Lys Val Glu Leu Ala Leu Glu Lys Lys Ser Ala
        50                  55                  60

CCT TCT CCT CTT ACC TAT CGC GGT ACG TGG ATG GTA CGT GAA GAC GGA        240
Pro Ser Pro Leu Thr Tyr Arg Gly Thr Trp Met Val Arg Glu Asp Gly
 65                 70                  75                  80

ATT GTC GAA CTC TCG CTT GTG TCC TCG GAG CAA TCG AAG GCA CCG CAC        288
Ile Val Glu Leu Ser Leu Val Ser Ser Glu Gln Ser Lys Ala Pro His
                85                  90                  95

GAG AAA GAG CTG TAC GAG CTG ATA GAC AGT AAC TCC GTT CGC TAC ATG        336
Glu Lys Glu Leu Tyr Glu Leu Ile Asp Ser Asn Ser Val Arg Tyr Met
                100                 105                 110

GGC GCT CCC GGC GCA GGA AAG CCT TCA AAG GAG ATG GCG CCG TTT TAC        384
Gly Ala Pro Gly Ala Gly Lys Pro Ser Lys Glu Met Ala Pro Phe Tyr
            115                 120                 125

GTG CTC AAA AAA ACA AAG AAA TAG                                        408
Val Leu Lys Lys Thr Lys Lys
            130                 135
```

(2) INFORMATION FOR SEQ ID NO:4:

(i) SEQUENCE CHARACTERISTICS:
        (A) LENGTH: 135 amino acids

-continued

```
      (B) TYPE: amino acid
      (D) TOPOLOGY: linear (ii) MOLECULE TYPE: protein (xi) SEQUENCE DESCRIPTION: SEQ ID NO:4:

Cys Val Ser Cys Thr Thr Val Cys Pro His Ala Gly Lys Ala Lys Ala
1               5                   10                  15

Glu Lys Val Glu Cys Ala Leu Lys Gly Gly Ile Phe Arg Gly Thr Leu
            20                  25                  30

Pro Ala Ala Asp Cys Pro Gly Ile Asp Thr Thr Val Thr Phe Asn Ala
        35                  40                  45

Asp Gly Thr Ala Gln Lys Val Glu Leu Ala Leu Glu Lys Lys Ser Ala
    50                  55                  60

Pro Ser Pro Leu Thr Tyr Arg Gly Thr Trp Met Val Arg Glu Asp Gly
65                  70                  75                  80

Ile Val Glu Leu Ser Leu Val Ser Ser Glu Gln Ser Lys Ala Pro His
                85                  90                  95

Glu Lys Glu Leu Tyr Glu Leu Ile Asp Ser Asn Ser Val Arg Tyr Met
            100                 105                 110

Gly Ala Pro Gly Ala Gly Lys Pro Ser Lys Glu Met Ala Pro Phe Tyr
            115                 120                 125

Val Leu Lys Lys Thr Lys Lys
130                 135
```

IMMUNOCHEMICAL DETERMINATION OF MULTIVALENT ANALYTES

BACKGROUND OF THE INVENTION

1. Field of the Invention

The present invention relates to an immunochemical method for qualitatively or quantitatively detecting an analyte. The method comprises contacting a first and second binding component with an analyte, followed by detecting the binding of the binding components to the analyte using known methods. Both binding components are prepared recombinantly in the same host using different vectors (V1 and V2) for expressing fusion proteins, with the first binding component being expressed as a fusion protein F1 in vector V1 and the second binding component being expressed as a fusion protein F2 in vector V2. The novel method, which can also be used for simultaneously determining several analytes, is more sensitive and has greater specificity than prior methods.

2. Description of the Related Art

Traditional immunological methods for diagnosing diseases associated with the formation of specific antibodies against disease-inducing agents, such as viruses, bacteria, parasites, allergens, autoantigens, or particular pharmaceuticals, are based on the ability of the antibodies to form complexes with antigenic structures of the disease-inducing agents.

In certain immunoassay methods, a sample to be tested, for example, for the presence of specific antibodies (analyte antibodies), is contacted with antigenic structures of the disease-inducing agents. Analyte antibodies present in the sample are bound as an immune complex to the antigenic structures of the disease-inducing agent immobilized on suitable known support materials. The analyte antibodies are then detected. Detection antibodies or other specific receptors (for example protein A) which are able to form a complex with the analyte antibody of the sample, or the analyte itself, can be used for the detection.

As a rule, the detection reagent is labeled thus enabling measurement the quantity of bound antibody. Examples of common labels are radioactive isotopes; enzymes; fluorescent, phosphorescent, or luminescent substances; substances having stable, unpaired electrons; erythrocytes; latex particles; magnetic particles; and metal sols.

Both homogeneous and heterogeneous (single-step and multi-step) test embodiments are known for carrying out these methods. For the heterogeneous embodiment, each step of the method is terminated with a separation process (washing step). However, heterogeneous immunoassays, which are very easy to implement, are not suitable for detecting all disease markers. Detection of some disease markers requires two-step or multi-step methods for technical reasons.

Double-antigen sandwich immunoassays or antibody bridge tests are known. In these methods, one or more solid-phase antigens, the specific analyte(s) to be detected, and one or more labeled conjugate antigens are contacted with each other. In the presence of specific analytes, complexes are formed which can be measured by means of the label on the conjugate antigen. The uniform presentation of the antigen, bridged by the antigen-binding domain of the analyte present in numerous copies, is crucial for the speed of formation and stability of the complexes.

Known embodiments include methods in which the antigens employed are: (1) isolated from naturally occurring prokaryotic or eukaryotic cells, (2) obtained from recombinantly altered prokaryotic or eukaryotic cells, or (3) obtained by chemical synthesis. These embodiments are very sensitive, in particular, when both of the binding components of the analyte are isolated from the same host. This is because for these cases the following are very similar: (1) antigen presentation, (2) the degree of glycosylation, and (3) the conformation of the two binding components.

A disadvantage of these embodiments is that host-specific constituents and/or impurities, present both in the immobilized phase and in the labeled phase, can lead to falsely positive reactions resulting from the possible presence of receptors against the host-specific constituents and/or impurities. Methods for suppressing such interference are known and comprise adding host-specific constituents and/or impurities that do not contain any binding components or antigenically active moieties thereof. However, this interference suppression is successful only for low-grade nonspecific reactions. A disadvantage of strong nonspecific interference, which requires the use of substantially greater quantities of interference-suppressing components, is that the specific signal is also strongly inhibited.

EP-0 307 149 discloses another method for avoiding interference due to host-specific constituents and/or impurities. This patent describes a double-antigen sandwich enzyme immunoassay based on recombinantly prepared proteins isolated from different host organisms. While an advantage of this method is that interference due to homologous impurities is either only slight or absent, a disadvantage is that the two receptors employed, R1 and R2, are folded and presented differently in the different host organisms. This leads to a less-specific reaction with the analyte to be detected and, consequently, the reaction has diminished sensitivity.

Another known option for avoiding non-specific interference in the double-antigen sandwich enzyme immunoassay is to construct the test using a recombinantly prepared protein and a synthetically prepared peptide. This option also has disadvantages in that the different folding and presentation of the two receptors R1 and R2 results in decreased sensitivity.

The advantage of mature protein expression for use in diagnosis is that the expressed antigen is not associated with any fusion moiety that can elicit nonspecific reactions. A disadvantage is that the strength of the expression of a protein which is heterologous to the host is often very low and therefore, purification techniques such as affinity chromatography are generally not effective in purifying the mature protein.

In contrast, expressing heterologous proteins as fusion proteins, together with a protein that is readily expressed in the host, frequently leads to higher rates of expression. Ideally, the fusion moiety also confers, in addition to the higher rate of expression, the ability of purifying the fusion protein using methods such as affinity chromatography. However, a disadvantage is that undesirable reactions can take place at the fusion moiety. Such reactions can be caused by, for example, the binding of substances to the fusion moiety where the substances have a binding affinity for the fusion moiety.

In practice, therefore, protein preparations that cause nonspecific reactions in diagnostic test systems are frequently obtained using both methods of expression, either due to the presence of a fusion moiety or, in the absence of a fusion moiety, due to the lack of an effective method for purifying the antigen, i.e., such as the use of affinity-chromatography.

There is a need in the art for a diagnostic test method and kit exhibiting high specificity and sensitivity for an analyte. The present invention satisfies this needs.

SUMMARY OF THE INVENTION

The present invention is directed to improving the performance of diagnostic test systems that use recombinantly prepared binding components. The present invention provides a highly specific and sensitive diagnostic kit and method that uses recombinantly prepared binding components. The novel method enables the use of fusion proteins without the disadvantages of poor specificity and sensitivity observed with the use of prior known methods.

Surprisingly, it was found that an immunochemical test system of high specificity and high sensitivity can be constructed. The system comprises two or more recombinantly prepared binding components, and the binding components are prepared in the same host using different vectors for expressing fusion proteins. Such a system is markedly superior in specificity and sensitivity to prior known embodiments in which two or more binding components are prepared in the same host using identical vectors for expressing fusion proteins.

For example, a double-antigen sandwich enzyme immunoassay using two binding components, F1 and F2, prepared in the same host with the aid of different vectors for expressing fusion proteins, is markedly more sensitive and specific than a double-antigen sandwich enzyme immunoassay in which F1 and F2 were prepared in the same host using the same vector for expressing fusion proteins.

The analyte to be detected according to the present invention can be, for example, an antibody which is induced by a disease-inducing agent, a vaccine, a multihapten, or a multivalent protein, such as the disease-inducing agent itself.

It is to be understood that both the foregoing general description and the following detailed description are exemplary and explanatory and are intended to provide further explanation of the invention as claimed. Other objects, advantages, and novel features will be readily apparent to those skilled in the art from the following detailed description of the invention.

DESCRIPTION OF THE FIGURES

FIG. 1 shows the recombinant protein pSEM-gp41 comprising a sequence of an antigen of human immunodeficiency virus (HIV).

FIG. 2 shows the recombinant protein pMAL-gp41 comprising a sequence of an antigen of human immunodeficiency virus (HIV).

FIG. 3 shows the plasmid pSEM-TpN17 comprising DNA encoding a *Treponema pallidum* antigen.

FIG. 4 shows the plasmid pMAL-TpN17 comprising DNA encoding a *Treponema pallidum* antigen.

DESCRIPTION OF THE PREFERRED EMBODIMENTS

Figure 1:
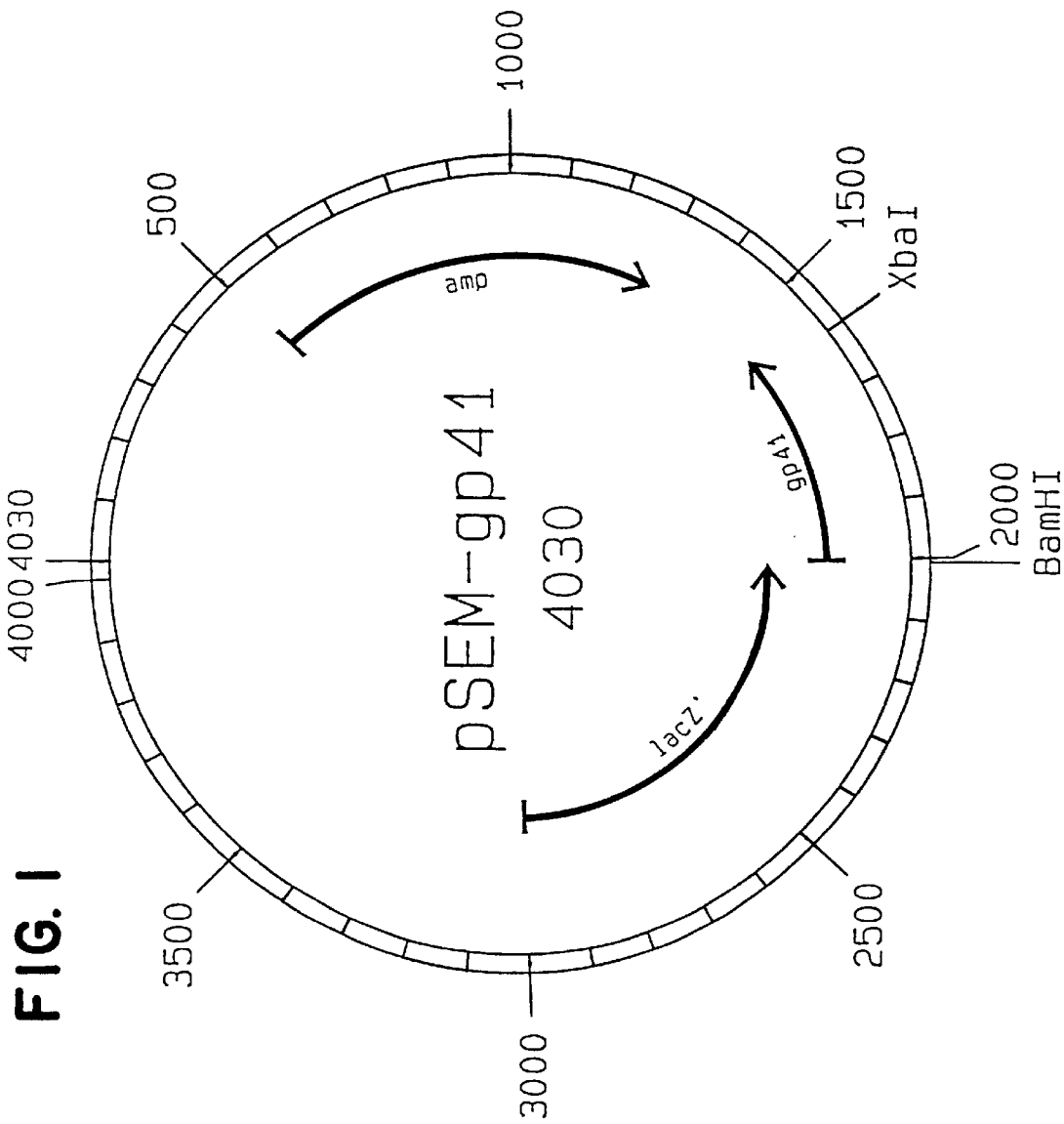
FIG. 1.

The invention is directed to an immunochemical method for qualitatively or quantitatively detecting an analyte in a sample. The method comprises contacting first and second binding components with the analyte, followed by detecting the binding of the binding components to the analyte using known methods. The two binding components are recombinantly prepared in the same host using different vectors (V1 and V2) for expressing fusion proteins, with the first binding component being expressed as a fusion protein F1 in vector V1 and the second binding component being expressed as a fusion protein F2 in vector V2.

Host systems according to the present invention are organisms capable of being transformed with a vector for expressing fusion proteins, capable of then being selected for the presence of the vector, and capable of replicating the vector and transcribing and translating the recombinant gene cloned in the vector. The host is preferably a bacterium or a yeast, and a particularly preferred embodiment comprises using *E. coli* as the host organism.

Preferred analytes are antibodies, with particularly preferred analytes being antibodies against viruses, bacteria, and parasites.

Immunochemical methods described above can be used for simultaneously determining different analytes, such as human immunodeficiency virus type 1 (HIV 1), human immunodeficiency virus type 2 (HIV 2), hepatitis A virus (HAV), hepatitis B virus (HBV), hepatitis C virus (HCV), or combinations thereof. Such embodiments are encompassed by the present invention.

Binding components according to the present invention are specific binding components having one or more bioaffinity binding sites for the analyte. Binding components or components thereof can be bound to the solid phase either directly or indirectly using bioaffinity interactions. Preferred solid phases are microtitration plates, magnetic particles, latex particles, or test elements containing a chemical matrix, such as test modules containing fibers or membranes. The binding components, or components thereof, can also be directly labeled (conjugate) or bound to a label using bioaffinity interactions.

Methods are known for preparing conjugates comprising a binding component and a label. Labels can be enzymes, such as peroxidase, alkaline phosphatase, galactosidase, or urease; haptens, such as biotin or digoxigenin; fluorescent compounds, such as FITC; luminescent compounds, such as acridinium esters or metal/chelate complexes; metal sols, such as gold; or particles, such as latex. Such conjugates, while retaining the bioaffinity function of their starting materials, can be prepared, for example, by linking using chemical reagents or by bioaffinity interaction. Hybrid molecules can also be produced by chemical synthesis, by the hybridoma technique, or by genetic manipulation methods.

The invention also relates to a reagent for use in the above-mentioned methods.

Combinations of binding components for specifically detecting analytes comprise:

F1: fusion protein from host system A, vector for expressing fusion proteins V1, and purified by method M1.

F2: fusion protein from host system A, vector for expressing fusion proteins V2, and purified by method M1 or M2.

Preferred combinations of binding components for specifically detecting analytes are:

F1: fusion protein from host system A, vector for expressing fusion proteins V1, and purified by method M1.

F2: fusion protein from host system A, vector for expressing fusion proteins V2, and purified by method M2.

Particularly preferred combinations of binding components for specifically detecting analytes are:

F1: fusion protein from host system A, which protein is insoluble in physiological buffers, vector for expressing fusion proteins V1, and purified by method M1.

F2: fusion protein from host system A, which protein is soluble in physiological buffers, vector for expressing fusion proteins V2, and purified by method M2.

Various methods for expressing recombinant proteins in a host system are known. Such methods are used to clone the DNA sequence encoding the desired antigen into a vector capable of replicating in the desired host. (*Current Protocols of Molecular Biology*, Supplement 30 (Wiley Interscience, 1995), hereby incorporated by reference.) The vector additionally encodes a selectable property, such as antibiotic resistance, which enables vector-harboring cells to be selected. The vector should also possess a promoter sequence at the 5' end of the gene for the recombinant antigen. The promoter sequence enables a host RNA polymerase, or an PNA polymerase, to initiate the copying of an mRNA for the recombinant antigen. Ideally, the promoter is specifically inducible. For example, the lac repressor system is inducible by adding IPTG. The vector should also contain a DNA sequence which terminates the transcription of the mRNA.

The translation start on the mRNA can be provided either by the vector system or by the recombinant antigen DNA itself. The skilled person can differentiate the mature expression of a protein without foreign moieties from the expression of a fusion protein. In the present instance, a fusion protein is defined as a fusion product composed of a peptide or protein encoded by the vector (fusion moiety) and the recombinant antigen (antigen moiety).

Vectors for expressing fusion proteins according to the present invention are nucleic acids capable of replicating in the suitable host and which encode a selectable property that makes it possible to select vector-harboring host organisms. Vectors for expressing fusion proteins ideally possess inducible promoters, downstream of which the genes for the recombinant antigens can be cloned. The presence of an inducible promoter enables the specific transcription and translation of the recombinant antigen.

Preferred vectors for expressing fusion proteins according to the present invention express the target protein fused to a constituent part which can be readily expressed in the respective host.

Particularly preferred vectors for expressing fusion proteins according to the present invention express the target protein fused to two different constituent parts which can be readily expressed in the respective host.

Most preferred vectors for expressing fusion proteins according to the present invention express the target protein fused to two different constituent parts that can be readily expressed in the respective host, with each respective constituent part enabling the use of different purification methods for the fusion protein.

Purification methods according to the present invention are methods that enable preparation of the target protein expressed in the host system in pure form. If secreted antigens are not prepared, the host organism must first be disrupted. Disruption methods are known, such as generating extreme pressure differences in a French press. The antigen can then be purified using known methods based on the physicochemical properties of the antigen, such as solubility, isoelectric point, charge, size, and electrophoretic mobility. Particularly extensive enrichment of the target protein can be achieved if the target protein is specifically and reversibly bound to a matrix so that the protein is accessible to purification by affinity chromatography.

In a preferred embodiment, the fusion protein F1 is primarily obtained from the soluble fraction of the host cell used to obtain the fusion protein, and the fusion protein F2 is primarily obtained from the insoluble fraction of the host cell used to obtain the fusion protein. In a more preferred embodiment, more than 50% of the fusion protein F1 is obtained from the soluble fraction and more than 50% of the fusion protein F2 is obtained from the insoluble fraction. In a most preferred embodiment, more than 80% of the fusion protein F 1 is obtained from the soluble fraction and more than 80% of the fusion protein F2 is obtained from the insoluble fraction.

The novel reagent can be used in a large number of human and veterinary diagnostic methods. Examples of such methods are single-step or multi-step tests for detecting antibodies of various immunoglobulin classes; antibodies against structural features of viruses, such as hepatitis A, B, and C, HIV 1, and HIV 2; antibodies against bacterial and parasitic pathogens, and of allergic diseases. Other examples include detecting disease-inducing agents, such as viruses (for example, hepatitis A, B, and C, HIV 1, and HIV 2), bacteria, parasites, and allergens, and also of disease markers (for example tumor markers), in single-step or multi-step detection methods.

Yet another preferred embodiment is a diagnostic kit useful for qualitatively or quantitatively detecting an analyte in a sample. Such a kit comprises a first and a second binding component for the analyte to be detected, wherein the first and second binding components are recombinantly prepared in the same host using different vectors, V1 and V2, with the first binding component being expressed as a fusion protein F1 in vector V1 and the second binding component being expressed as a fusion protein F2 in vector V2. In addition, the kit comprises standard components known in the art, such as a container, reagents, etc.

Another diagnostic kit according to the invention comprises materials for qualitatively or quantitatively detecting one or more additional analytes. In addition to the components given above, such a kit comprises two binding components for the second reagent, wherein the binding components are recombinantly prepared in the same host using different vectors for expressing fusion proteins. A preferred embodiment is directed to a kit in which the binding components of the different analytes are expressed in different hosts.

The following examples are given to illustrate the present invention. It should be understood, however, that the invention is not to be limited to the specific conditions or details described in these examples.

EXAMPLE 1

Enzyme Immunoassay for Detecting HIV 1 Antibodies

1(a) Preparation of the Recombinant Proteins pMAL-gp41 and pSEM-gp41

Figure 2:
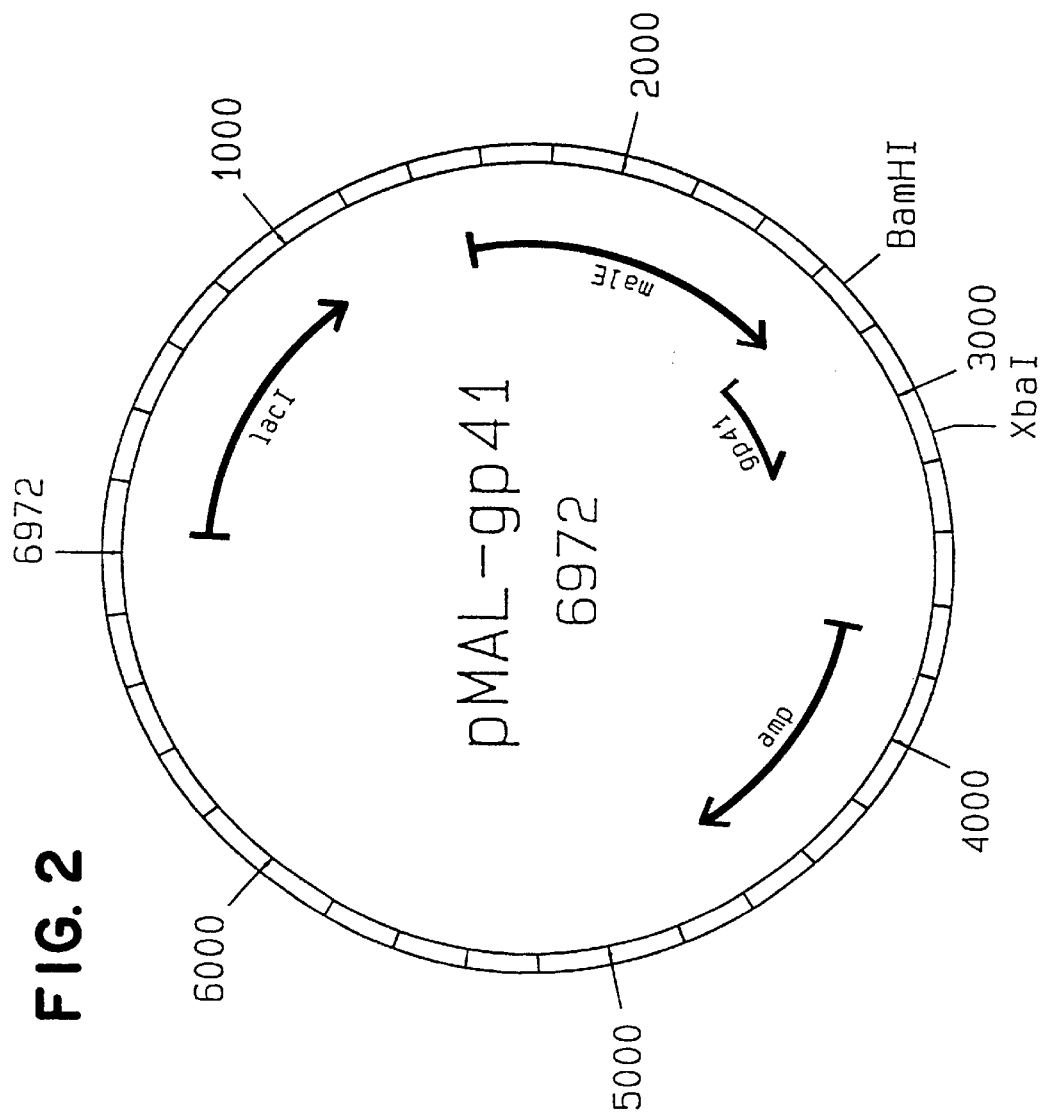
FIG. 2.

DNA encoding the HIV antigens was prepared by PCR using the HIV strain HIV1-BH10 as the template. The amplified fragment encompassed bp7209–bp7508 (SEQ ID NO: 1). Inserting the restriction cleavage sites BamHI at the 5' end and XbaI at the 3' end of the fragment enabled the fragment to be cloned into the expression vectors pMAL-c2 (New England Biolabs) and pSEM (Knapp et al., *Biotechniques,* 8(3):280–281 (1990)). The recombinant proteins were expressed and purified. For pSEM-gp41 (FIG. 1), the recombinant protein was purified by differential urea extraction in 7M urea from the inclusion bodies, followed by purification by gel chromatography. For pMAL-gp41 (FIG. 2), the recombinant protein was purified by affinity chromatography in accordance with the manufacturer's instructions. Both recombinant proteins were adjusted to a concentration of 1 g/l. The pMAL-gp41 protein was present in 50 mM sodium carbonate, pH 8.0, while the pSEM-gp41 protein was present in 50 mM sodium carbonate, 6 M urea, pH 8.0.

1(b) Preparation of Solid Phase I (Novel System)

Type B microtitration plates (Nunc, Roskilde, Denmark) were incubated at 4° C. for 24 hours, with coating solution (600 μg of recombinant pSEM-gp41/1 (prepared as described in Example 1(a) in 50 mM sodium carbonate buffer, pH 9.5). 100 μl of the coating solution was present in each well. The wells of the microtitration plates were then washed three times with 300 μl of washing solution (50 mM Tris, 0.1% Tween 20, pH 7.2) on each occasion. The microtitration plates, which are dried over silica gel, are stable for about 1 year when air is excluded.

1(c) Preparation of Solid Phase II (Reference System)

Type B microtitration plates (Nunc, Roskilde, Denmark) were incubated at 4° C. for 24 hours with coating solution (600 μg of recombinant pMAL-gp41/1 (prepared as described in example 1(a) in 50 mM sodium carbonate buffer, pH 9.5). 100 μl of the coating solution was present in each well. The wells of the microtitration plates were then washed three times with 300 μl of washing solution (50 mm Tris, 0.1% Tween 20, pH 7.2) on each occasion. The microtitration plates, which are dried over silica gel, are stable for about 1 year when air is excluded.

1(d) Preparation of the Conjugate

A 10-fold molar excess of N-γ-maleimidobutyryl-succinimide was added to 10 mg of recombinant pMAL-gp41 (prepared as described in Example 1(a)) and the mixture was incubated at room temperature for 1 hour. The unreacted heterobifunctional reagent was separated off by gel filtration (Sephadex G-25) using 100 mM sodium phosphate, 5 mM nitriloacetic acid, pH 6.0.

10 mg of horseradish peroxidase (Boehringer Mannheim, Mannheim, FRG) was incubated in 10 ml of 10 mM sodium phosphate, 100 mM sodium chloride, pH 8.0, together with a 100-fold molar excess of 2-iminothiolane at room temperature for 1 hour. Free modification reagent was subsequently removed by gel filtration (Sephadex G-25) using 100 mM sodium phosphate, 5 mM nitriloacetic acid, pH 6.0.

The two eluates (i.e., SH-activated peroxidase and maleimide-modified HIV 1 protein) were combined and incubated at room temperature overnight. After the reaction was stopped with 1/10 vol of 100 mM N-ethylmaleimide, the conjugate was purified from non-reacted HIV 1 protein using gel filtration (Sephadex G-25). After the conjugate is concentrated (2 mg/ml), it was stored at −20° C.

1(e) Enzyme immunoassay for Detecting HIV 1 Antibodies

An enzyme immunoassay for detecting anti-HIV 1 antibodies is carried out as follows: 25 μl of sample buffer (0.3 M Tris/HCl, 1% albumin, 2% Tween 20, pH 7.2) was incubated at 37° C. for 30 minutes, with 100 μl of human serum in the wells of the microtitration plates prepared as described in Examples 1(a) and 1(b), above. After the plates were washed 4 times with 50 mM PBS, 0.1% Tween 20, 125 μl of the conjugate prepared as described in Example 1(c) (1:1000 in 0.1 M Tris/HCl, 1 mM glycine, 0.2% albumin, 0.4% Pluronic F64, pH 8.1) is pipetted into the wells. The 30-minute incubation (+37° C.) is terminated by four further washing steps. The bound peroxidase activity, which correlates directly with the quantity of bound anti-HIV 1 antibodies, is determined by adding $H_2O_2$/tetramethylbenzidine. After 30 minutes at room temperature, substrate conversion is stopped by adding 0.5 M sulfuric acid. The extinction is determined at 450 nm.

Anti-HIV 1-positive sera, normal anti-HIV-negative sera, and selected anti-HIV-negative sera which are falsely positive in the reference system were investigated both in the reference system and in the novel enzyme immunoassay. The results (extinction units) of the investigation are presented in Table 1.

TABLE 1

| Sample Designation | Anti-HIV Status | Dilution | Reference System | Novel System |
|---|---|---|---|---|
| negative control | negative | native | 0.098 | 0.103 |
| positive control | positive | 1:4000 | 1.575 | 1.412 |
| 9111/39 | positive | 1:100 | 1.211 | 1.653 |
| 9111/39 | positive | 1:200 | 0.520 | 0.886 |
| 9111/46 | positive | 1:50 | 0.528 | 0.927 |
| 9111/46 | positive | 1:100 | 0.310 | 0.489 |
| 9205/19 | positive | 1:8000 | 0.906 | 0.877 |
| BS 17-1 | negative | native | 0.058 | 0.064 |
| BS 17-2 | negative | native | 0.071 | 0.070 |
| BS 17-3 | negative | native | 0.066 | 0.051 |
| BS 17-4 | negative | native | 0.066 | 0.059 |
| BS 17-5 | negative | native | 0.082 | 0.074 |
| BS 1-5 | negative | native | 1.876 | 0.089 |
| BS 1-17 | negative | native | 2.077 | 0.078 |
| BS 1-33 | negative | native | >2.5 | 0.075 |
| BS 1-59 | negative | native | >2.50 | 0.091 |

There are marked differences in signal formation in the two test systems, particularly for the anti-HIV-negative samples. Anti-HIV-positive sera react in a comparable manner in the two test systems.

EXAMPLE 2

Enzyme Immunoassay for Detecting *T. pallidum* Antibodies

2(a) Preparation of the Recombinant Antigens

Figure 3:
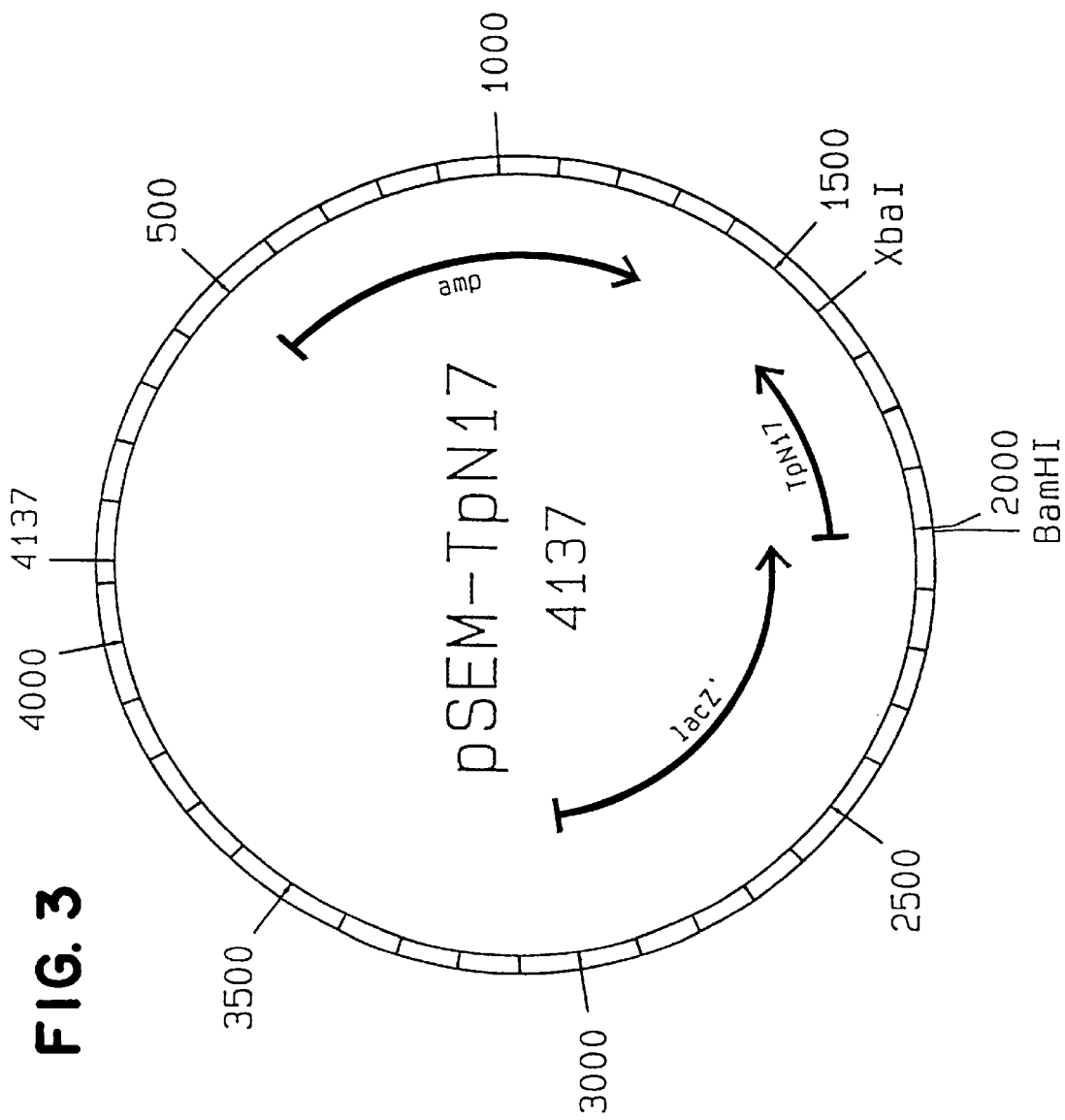
FIG. 3.
Figure 4:
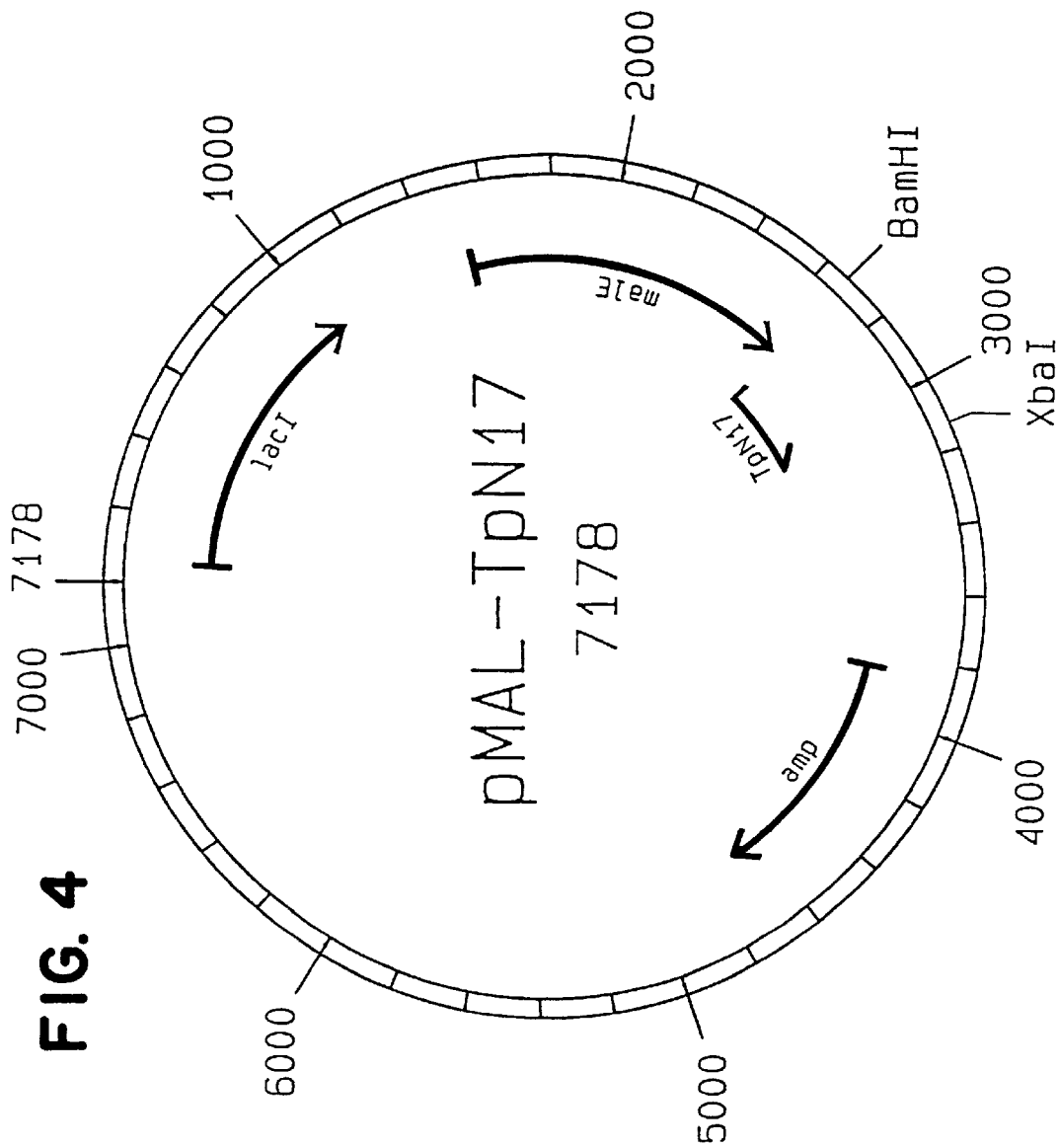
FIG. 4.

DNA encoding *T. pallidum* antigens was prepared via PCR using genomic DNA of the *T. pallidum* strain Nichols as the template. The PCR primers were designed such that the entire open reading frame of the protein TpN17 (SEQ ID NO: 3) was amplified and a BamHI cleavage site and an XbaI cleavage site were introduced at the 5' and 3' ends, respectively, of the amplificate. The *T. pallidum* antigen DNA was then cloned into the expression vectors pMAL-c2 (New England Biolabs) and pSEM (Knapp et al., *Biotechniques*, 8(3):280–281 (1990)) using the restriction endonucleases BamHI and XbaI. The recombinant proteins were expressed and purified. For pSEM-TpN17 (FIG. 3), the recombinant protein was purified by differential urea extraction, in 7M urea, from the inclusion bodies followed by gel chromatography purification. For pMAL-TpN17 (FIG. 4), the recombinant protein was purified by affinity chromatography in accordance with the manufacturer's instructions. The proteins were adjusted to a concentration of 1 g/l. The pMAL-TpN17 protein was present in 50 mm sodium carbonate, pH 8.0, while the pSEM-TpN17 protein was present in 50 mM sodium carbonate, 6 M urea, pH 8.0.

2(b) Preparation of Solid Phase I (Novel System)

Type B microtitration plates (Nunc, Roskilde, Denmark) were incubated at 4° C. for 24 hours with coating solution (3 mg of recombinant pSEM-Tpn 17/1 (prepared as described in Example 2(a) in 50 mM sodium carbonate buffer, pH 9.5). 100 μl of the coating solution was present in each well. The wells of the microtitration plates were then washed three times with 300 μl of washing solution (50 mM Tris, 0.1% Tween 20, pH 7.2) on each occasion. The microtitration plates, which are dried over silica gel, are stable for about 1 year when air is excluded.

2(c) Preparation of Solid Phase II (Reference System)

Type B microtitration plates (Nunc, Roskilde, Denmark) were incubated at 4° C. for 24 hours with coating solution (3 mg of recombinant pMAL-TpN17/1 (prepared as described in Example 2(a) in 50 mM sodium carbonate buffer, pH 9.5). 100 μl of the coating solution was present in each well. The wells of the microtitration plates were then washed three times with 300 μl of washing solution (50 mM Tris, 0.1% Tween 20, pH7.2) on each occasion. The microtitration plates, which are dried over silica gel, are stable for about 1 year when air is excluded.

2(d) Preparation of the Conjugate

A 10-fold molar excess of N-y-maleimidobutyryl-succinimide was added to 10 mg of recombinant pMAL-TpN17 (preparation as described in Example 2(a)) and the mixture was incubated at room temperature for 1 hour. The unreacted heterobifunctional reagent was separated off by gel filtration (Sephadex G-25) using 100 mM sodium phosphate, 5 mM nitriloacetic acid, pH 6.0.

10 mg of horseradish peroxidase (Boehringer Mannheim, Mannheim, FRG) was incubated in 10 ml of 10 mM sodium phosphate, 100 mm sodium chloride, pH 8.0, together with a 100-fold molar excess of 2-iminothiolane at room temperature for 1 hour. Free modification reagent was then removed by gel filtration (Sephadex G-25) using 100 mM sodium phosphate, 5 mM nitriloacetic acid, pH 6.0.

The eluates (SH-activated peroxidase and maleimide-modified *T. pallidum* protein) were combined and incubated at room temperature overnight. After the reaction was stopped with 1/10 vol of 100 mM N-ethylmaleimide, the conjugate was purified from unreacted *T. pallidum* protein by gel filtration (Sephadex G-25). After concentration (2 mg/ml), the conjugate was stored at −20° C.

2(e) Enzyme Immunoassay for Detecting *T. pallidum* Antibodies

An enzyme immunoassay for detecting anti-*T. pallidum* antibodies was carried out as follows: 25 μl of sample buffer (0.3 M Tris/HCl, 1% alburrin, 2% Tween 20, pH 7.2) was incubated at 37° C. for 30 minutes, with 100 μl of human serum in the wells of the microtitration plates prepared as described in Examples 2(b) and 2(c). After the plates were washed four times with 50 mM PBS, 0.1% Tween 20, 125 μl of the conjugate prepared as described in Example 1(c) (1:1000 in 0.1 M Tris/HCl, 1 mM glycine, 0.2% albumin, 0.4% Pluronic F64, pH 8.1) was pipetted into the wells. The 30-minute incubation (+37° C.) was terminated with 4 further washing steps. The bound peroxidase activity, which correlates directly with the quantity of bound anti-*T. pallidum* antibodies, was determined by adding $H_2O_2$/tetramethylbenzidine. After 30 minutes at room temperature, substrate conversion was stopped by adding 0.5 m sulfuric acid. The extinction was determined at 450 nm.

Anti-*T. pallidum*-positive sera and anti-*T. pallidum*-negative sera were investigated both in the reference system and in the novel enzyme immunoassay. The results (extinction units) of the investigation are presented in Table 2.

TABLE 2

| Sample Designation | Anit- T. pallidum Status | Dilution | Novel System | Reference System |
|---|---|---|---|---|
| Boston Biomedical BM696640 | positive | native | >2.5 | >2.5 |
| Boston Biomedical BM69631 | positive | native | >2.5 | >2.5 |
| Boston Biomedical BM69232 | positive | native | >2.5 | >2.5 |
| Boston Biomedical BM69641 | positive | native | >2.5 | >2.5 |
| Boston Biomedical BM69642 | positive | native | >2.5 | >2.5 |
| Boston Biomedical BM69639 | positive | native | >2.5 | >2.5 |
| Boston Biomedical BM68378 | positive | native | >2.5 | >2.5 |
| Boston Biomedical BM69624 | positive | native | >2.5 | >2.5 |
| Boston Biomedical BM69625 | positive | native | >2.5 | >2.5 |
| Boston Biomedical BM69214 | positive | native | >2.5 | >2.5 |
| Boston Biomedical BM69577 | positive | native | >2.5 | >2.5 |
| Blood donor #40 | negative | native | 0.015 | 0.068 |
| Blood donor #49 | negative | native | 0.033 | 0.036 |
| Blood donor #50 | negative | native | 0.029 | 0.073 |
| Blood donor #51 | negative | native | 0.012 | 0.050 |
| Blood donor #52 | negative | native | 0.024 | 0.260 |
| Blood donor #53 | negative | native | 0.090 | 0.035 |
| Blood donor #54 | negative | native | 0.012 | 0.041 |
| Blood donor #55 | negative | native | 0.015 | 0.066 |
| Blood donor #56 | negative | native | 0.013 | 0.240 |
| Blood donor #57 | negative | native | 0.019 | 0.038 |
| Blood donor #58 | negative | native | 0.013 | 0.061 |
| Blood donor #59 | negative | native | 0.010 | 0.035 |
| Blood donor #60 | negative | native | 0.008 | 0.122 |
| Blood donor #61 | negative | native | 0.013 | 0.050 |
| Blood donor #62 | negative | native | 0.023 | 0.068 |
| Blood donor #63 | negative | native | 0.036 | 0.067 |
| Blood donor #64 | negative | native | 0.022 | 0.033 |
| Blood donor #65 | negative | native | 0.017 | 0.044 |
| Blood donor #66 | negative | native | 0.047 | 0.079 |
| Blood donor #67 | negative | native | 0.017 | 0.056 |
| Blood donor #68 | negative | native | 0.006 | 0.044 |
| Blood donor #69 | negative | native | 0.005 | 0.073 |
| Blood donor #70 | negative | native | 0.009 | 0.069 |
| Blood donor #71 | negative | native | 0.009 | 1.637 |
| Blood donor #72 | negative | native | 0.038 | 0.027 |
| Blood donor #73 | negative | native | 0.008 | 0.029 |
| Blood donor #74 | negative | native | 0.017 | 0.029 |
| Blood donor #75 | negative | native | 0.011 | 0.336 |
| Blood donor #76 | negative | native | 0.008 | 0.033 |
| Blood donor #77 | negative | native | 0.008 | 0.056 |
| Blood donor #78 | negative | native | 0.023 | 0.058 |
| Blood donor #79 | negative | native | 0.005 | 0.118 |
| Blood donor #80 | negative | native | 0.009 | 0.438 |
| Blood donor #81 | negative | native | 0.041 | 0.870 |
| Blood donor #82 | negative | native | 0.007 | 0.059 |
| Blood donor #83 | negative | native | 0.012 | 0.029 |

Marked differences in signal formation can be seen in the two test systems, particularly in the case of anti-*T. pallidum*-negative samples. While some anti-*T. pallidum*-negative sera give a falsely positive reaction in the reference system, they do not do so in the novel system. Anti-*T. pallidum*-positive sera react in a comparable manner in both test systems.

SEQ ID NOS 1 & 2:

LOCUS:       HIVBHIO2 8932 bp ss-RNA    VRL
DEFINITION: Human immunodeficiency virus type 1, isolate BHIO, genome.
ACCESSION:  M15654, K02008;K02009, K02010
KEYWORDS:   TAR region; acquired immune deficiency syndrome; env protein;
            gag protein; long terminal repeat (LTR) ; pol protein; polypro-
            tein;
            proviral gene; reverse transcriptase; trans-activator

```
      TTATTGTCTGGTATAGTGCAGCAGCAGAACAATTTGCTGAGGGCTATTGAGGCGCAACAG
7209----------------------------------------------------------------7268
      AATAACAGACCATATCACGTCGTCGTCTTGTTAAACGACTCCCGATAACTCCGCGTTGTC
      L   L   S   G   I   V   Q   Q   Q   N   N   L   L   R   A   I   E   A   Q   Q

CATCTGTTGCAACTCACAGTCTGGGGCATCAAGCAGCTCCAGGCAAGAATCCTGGCTGTG
7269----------------------------------------------------------------7328
      GTAGACAACGTTGAGTGTCAGACCCCGTAGTTCGTCGAGGTCCGTTCTTAGGACCGACAC
      H   L   L   Q   L   T   V   W   G   I   K   Q   L   Q   A   R   I   L   A   V

GAAAGATACCTAAAGGATCAACAGCTCCTGGGGATTTGGGGTTGCTCTGGAAAACTCATT
7329----------------------------------------------------------------7388
      CTTTCTATGGATTTCCTAGTTGTCGAGGACCCCTAAACCCCAACGAGACCTTTTGAGTAA
      E   R   Y   L   K   D   Q   Q   L   L   G   I   W   G   C   S   G   K   L   I

TGCACCACTGCTGTGCCTTGGAATGCTAGTTGGAGTAATAAATCTCTGGAACAGATTTGG
7389----------------------------------------------------------------7448
      ACGTGGTGACGACACGGAACCTTACGATCAACCTCATTATTTAGAGACCTTGTCTAAACC
      C   T   T   A   V   P   W   N   A   S   W   S   N   K   S   L   E   Q   I   W

AATAACATGACCTGGATGGAGTGGGACAGAGAAATTAACAATTACACAAGCTTAATACAC
7449----------------------------------------------------------------7508
      TTATTGTACTGGACCTACCTCACCCTGTCTCTTTAATTGTTAATGTGTTCGAATTATGTG
      N   N   M   T   W   M   E   W   D   R   E   I   N   N   Y   T   S   L   I   H
```

SEQ ID NOS 3 & 4:

LOCUS:      TRP17LPOPR 660 bp DNA    BCT
DEFINITION: Treponemapallidum 17 kDa Iipoprotein gene, complete cds.
ACCESSION:  M74825
KEYWORDS:   lipoprotein.
SOURCE:     Theponema pallidum (strain Nichols, sub-species pallidum) DNA.
ORGANISM:   Treponema pallidum

```
 TGTGTCTCGTGCACAACCGTGTGTCCGCACGCCGGGAAGGCCAAAGCGGAAAAGGTAGAG
163---------------------------------------------------------------222
 ACACAGAGCACGTGTTGGCACACAGGCGTGCGGCCCTTCCGGTTTCGCCTTTTCCATCTC
 C   V   S   C   T   T   V   C   P   H   A   G   K   A   K   A   E   K   V   E

TGCGCGTTGAAGGGAGGTATCTITCGGGGTACGCTACCTGCGGCCGATTGCCCGGGAATC
223---------------------------------------------------------------282
 ACGCGCAACTTCCCTCCATAGAAAGCCCCATGCGATGGACGCCGGCTAACGGGCCCTTAG
 C   A   L   K   G   G   I   F   R   G   T   L   P   A   A   D   C   P   G   I

GATACGACTGTGACGTTCAACGCGGATGGCACTGCGCAAAAGGTAGAGCTTGCCCTTGAG
283---------------------------------------------------------------342
 CTATGCTGACACTGCAAGTTGCGCCTACCGTGACGCGTTTTCCATCTCGAACGGGAACTC
 D   T   T   V   T   F   N   A   D   G   T   A   Q   K   V   E   L   A   L   E

AAGAAGTCGGCACCTTCTCCTCTTACCTATCGCGGTACGTGGATGGTACGTGAAGACGGA
343---------------------------------------------------------------402
 TTCTTCAGCCGTGGAAGAGGAGAATGGATAGCGCCATGCACCTACCATGCACTTCTGCCT
 K   K   S   A   P   S   P   L   T   Y   R   G   T   W   M   V   R   E   D   G

ATTGTCGAACTCTCGCTTGTGTCCTCGGAGCAATCGAAGGCACCGCACGAGAAAGAGCTG
403---------------------------------------------------------------462
 TAACAGCTTGAGAGCGAACACAGGAGCCTCGTTAGCTTCCGTGGCGTGCTCTTTCTCGAC
 I   V   E   L   S   L   V   S   S   E   Q   S   K   A   P   H   E   K   E   L

TACGAGCTGATAGACAGTAACTCCGTTCGCTACATGGGCGCTCCCGGCGCAGGAAAGCCT
463---------------------------------------------------------------522
 ATGCTCGACTATCTGTCATTGAGGCAAGCGATGTACCCGCGAGGGCCGCGTCCTTTCGGA
 Y   E   L   I   D   S   N   S   V   R   Y   M   G   A   P   G   A   G   K   P

TCAAAGGAGATGGCGCCGTTTTACGTGCTCAAAAAAACAAAGAAATAG
523-----------------------------------------------570
```

```
                    -continued
AGTTTCCTCTACCGCGGCAAAATGCACGAGTTTTTTTGTTTCTTTATC
 S   K   E   M   A   P   F   Y   V   L   K   K   T   K   K   *
```

Priority application Germany 197 23 463. 1, filed on Jun. 4, 1997, including the specification, drawings, claims, and abstract, is hereby incorporated by reference.

It will be apparent to those skilled in the art that various modifications and variations can be made in the compositions, methods, and uses of the present invention without departing from the spirit or scope of the invention. Thus, it is intended that the present invention cover the modifications and variations of this invention provided they come within the scope of the appended claims and their equivalents.

---

We claim:

1. An immunochemical method for qualitatively or quantitatively detecting an analyte in a sample comprising:
   (a) contacting a first and a second binding component with an analyte, wherein said first and second binding components are obtained by recombinant preparation in the same host, wherein said first and second binding components are fusion proteins that each comprise a fusion moiety and a binding moiety and wherein said binding moieties of said first and second binding component are the same and said fusion moieties of said first and second binding component are different; and
   (b) detecting said analyte.

2. The method of claim 1, wherein one or more of said binding components is immobilized on a solid phase.

3. The method of claim 2, wherein said solid phase is used in a double-antigen sandwich immunoassay method.

4. The method of claim 1, wherein said host is selected from the group consisting of a eukaryotic organism and a prokaryotic organism.

5. The method of claim 4, wherein said host is a bacterium.

6. The method of claim 5, wherein said bacterium is *E. coli*.

7. The method of claim 1, wherein said first binding component is primarily obtained from a soluble fraction of said host and said second binding component is primarily obtained from an insoluble fraction of said host.

8. The method of claim 7, wherein more than 50% of said first binding component is obtained from said soluble fraction of said host and more than 50% of said second binding component is obtained from said insoluble fraction of said host.

9. The method of claim 8, wherein more than 80% of said first binding component is obtained from said soluble fraction of said host and more than 80% of said second binding component is obtained from said insoluble fraction of said host.

10. The method of claim 1, wherein said first binding component is obtained by recombinant expression in a pSEM vector and said second binding component is obtained by recombinant expression in a pMAL vector.

11. The method of claim 1, wherein said analyte is an antibody and wherein said binding moiety is an antigen.

12. The method of claim 11, wherein said antibody is directed against viruses, bacteria, parasites, allergens, autoantigens, pharmaceuticals, a component of a virus, a component of a bacterium, a component of a parasite, a component of an allergen, a component of an autoantigen, a component of a pharmaceutical, or a mixture thereof.

13. The method of claim 12, wherein said antibody is directed against HIV 1, HIV 2, *Treponema pallidum*, or a combination thereof.

14. The method of claim 1, wherein said first binding component is immobilized on a solid phase and said second binding component is labeled.

15. A kit for qualitatively or quantitatively detecting an analyte in a sample comprising a first and a second binding component for said analyte to be detected, wherein said first and second binding components are obtained by recombinant preparation in the same host, wherein said first and second binding components are fusion proteins that each comprise a fusion moiety and a binding moiety and wherein said binding moieties of said first and second binding component are the same and said fusion moieties of said first and second binding component are different.

16. The kit of claim 15, further comprising a first and a second binding component for qualitatively or quantitatively detecting a second different analyte, wherein said two binding components of each different analyte are obtained by recombinant preparation in the same host, wherein said first and second binding components are fusion proteins that each comprise a fusion moiety and a binding moiety and wherein said binding moieties of said first and second binding component of each different analyte are the same and said fusion moieties of said first and second binding component of each different analyte are different.

17. The kit of claim 16, wherein said binding components of said different analytes are expressed in a different host.

18. An immunochemical method for qualitatively or quantitatively detecting two or more different analytes in a sample comprising:
(a) contacting a first and a second binding component, per different analyte, with two or more different analytes, wherein said first and second binding components of each different analyte are recombinantly prepared in the same host system, wherein said first and second binding components are fusion proteins that each comprise a fusion moiety and a binding moiety and wherein said binding moieties of said first and second binding component of each different analyte are the same and said fusion moieties of said first and second binding component of each different analyte are different; and
(b) detecting said two or more analytes.

19. The method of claim 18, wherein said binding components for each of said different analytes are obtained by recombinant expression in a different host.

20. The method of claim 18, wherein said first binding component is immobilized on a solid phase and said second binding component is labeled.

21. An immunochemical method for qualitatively or quantitatively detecting an analyte in a sample comprising:
(a) contacting a first and a second binding component with an analyte, wherein said first and second binding components are fusion proteins that each comprise a fusion moiety and a binding moiety and wherein said binding moieties of said first and second binding component are the same and said fusion moieties of said first and second binding component are different; and
(b) detecting said analyte.

* * * * *